(12) United States Patent
Cuckler et al.

(10) Patent No.: US 8,696,754 B2
(45) Date of Patent: Apr. 15, 2014

(54) REVISION PATELLA PROSTHESIS

(75) Inventors: John M. Cuckler, Birmingham, AL (US); Christopher Peters, Park City, UT (US)

(73) Assignee: Biomet Manufacturing, LLC, Warsaw, IN (US)

( * ) Notice: Subject to any disclaimer, the term of this patent is extended or adjusted under 35 U.S.C. 154(b) by 1130 days.

(21) Appl. No.: 12/203,575

(22) Filed: Sep. 3, 2008

(65) Prior Publication Data

US 2010/0057211 A1 Mar. 4, 2010

(51) Int. Cl.
*A61F 2/38* (2006.01)

(52) U.S. Cl.
USPC ........................ 623/20.2; 623/20.18

(58) Field of Classification Search
None
See application file for complete search history.

(56) References Cited

U.S. PATENT DOCUMENTS

| | | | |
|---|---|---|---|
| 3,927,423 A * | 12/1975 | Swanson | 623/20.2 |
| 3,964,106 A | 6/1976 | Hutter, Jr. et al. | |
| 4,041,550 A | 8/1977 | Frazier | |
| 4,158,894 A | 6/1979 | Worrell | |
| 4,759,768 A | 7/1988 | Hermann et al. | |
| 4,913,157 A | 4/1990 | Pratt, Jr. et al. | |
| 5,011,496 A | 4/1991 | Forte et al. | |
| 5,019,104 A | 5/1991 | Whiteside et al. | |
| 5,181,924 A | 1/1993 | Gschwend et al. | |
| 5,197,986 A | 3/1993 | Mikhail | |
| 5,236,461 A | 8/1993 | Forte | |
| 5,236,462 A * | 8/1993 | Mikhail | 623/20.2 |
| 5,314,480 A * | 5/1994 | Elloy et al. | 623/20.2 |
| 5,358,529 A | 10/1994 | Davidson | |
| 5,383,937 A | 1/1995 | Mikhail | |
| 5,405,395 A | 4/1995 | Coates | |
| 5,425,775 A | 6/1995 | Kovacevic et al. | |
| 5,480,443 A | 1/1996 | Elias | |
| 5,522,901 A | 6/1996 | Thomas et al. | |
| 5,571,196 A | 11/1996 | Stein | |
| 5,609,640 A | 3/1997 | Johnson | |
| 5,609,644 A | 3/1997 | Ashby et al. | |
| 5,658,348 A | 8/1997 | Rohr, Jr. | |
| 5,702,465 A | 12/1997 | Burkinshaw | |

(Continued)

FOREIGN PATENT DOCUMENTS

| | | |
|---|---|---|
| EP | 0307654 A2 | 3/1989 |
| FR | 2642301 A1 | 8/1990 |

OTHER PUBLICATIONS

European Search Report mailed Nov. 20, 2009 for EP09169382 claiming benefit of U.S. Appl. No. 12/203575, filed Sep. 3, 2008.

(Continued)

*Primary Examiner* — Thomas J Sweet
*Assistant Examiner* — Rebecca Preston
(74) *Attorney, Agent, or Firm* — Harness, Dickey

(57) ABSTRACT

A knee prosthesis assembly can comprise a patella prosthesis adapted to be secured to a natural patella portion having an anterior surface and a posterior surface. An articulating portion can have a posteriorly facing portion and an anteriorly facing portion. The posteriorly facing portion can have a spherical articular surface. A porous portion can have a first portion that engages the anteriorly facing portion and a second portion that engages the natural patella portion. A fastener can pass entirely through a passage formed at a centermost portion of the natural patella portion from the anterior surface to the posterior surface and into a bore defined in the centermost portion of the porous portion to securably engage the porous portion.

21 Claims, 3 Drawing Sheets

(56) References Cited

U.S. PATENT DOCUMENTS

| | | |
|---|---|---|
| 5,702,467 A | 12/1997 | Gabriel et al. |
| 5,725,591 A | 3/1998 | DeCarlo, Jr. et al. |
| 5,876,455 A | 3/1999 | Harwin |
| 5,885,298 A | 3/1999 | Herrington et al. |
| 5,951,603 A | 9/1999 | O'Neil et al. |
| 5,957,979 A | 9/1999 | Beckman et al. |
| 6,010,534 A | 1/2000 | O'Neil et al. |
| 6,053,945 A | 4/2000 | O'Neil et al. |
| 6,146,423 A | 11/2000 | Cohen et al. |
| 6,315,798 B1 | 11/2001 | Ashby et al. |
| 6,416,553 B1 | 7/2002 | White et al. |
| 6,572,655 B1 * | 6/2003 | Johnson .................. 623/22.36 |
| 6,602,292 B2 | 8/2003 | Burkinshaw |
| 6,616,696 B1 | 9/2003 | Merchant |
| 6,620,198 B2 | 9/2003 | Burstein et al. |
| 6,679,917 B2 * | 1/2004 | Ek .................. 623/20.14 |
| 6,702,821 B2 | 3/2004 | Bonutti |
| 6,770,078 B2 | 8/2004 | Bonutti |
| 6,800,094 B2 | 10/2004 | Burkinshaw |
| 6,855,150 B1 | 2/2005 | Linehan |
| 6,923,831 B2 | 8/2005 | Fell et al. |
| 7,048,741 B2 | 5/2006 | Swanson |
| 2002/0128719 A1 | 9/2002 | Burkinshaw |
| 2003/0060883 A1 | 3/2003 | Fell et al. |
| 2003/0088315 A1 | 5/2003 | Supinski |
| 2003/0125745 A1 * | 7/2003 | Tseng et al. .................. 606/73 |
| 2004/0064192 A1 | 4/2004 | Bubb |
| 2004/0143336 A1 | 7/2004 | Burkinshaw |
| 2004/0143337 A1 | 7/2004 | Burkinshaw |
| 2004/0236428 A1 | 11/2004 | Burkinshaw et al. |
| 2005/0033424 A1 | 2/2005 | Fell |
| 2005/0177240 A1 * | 8/2005 | Blain .................. 623/17.15 |
| 2006/0100714 A1 | 5/2006 | Ensign |
| 2006/0241776 A1 | 10/2006 | Brown et al. |
| 2006/0241781 A1 | 10/2006 | Brown et al. |
| 2007/0129809 A1 | 6/2007 | Meridew et al. |
| 2007/0135924 A1 | 6/2007 | Verhoogen |
| 2007/0173948 A1 | 7/2007 | Meridew et al. |
| 2007/0196230 A1 | 8/2007 | Hamman et al. |
| 2007/0250175 A1 | 10/2007 | Meridew et al. |
| 2007/0265708 A1 | 11/2007 | Brown et al. |
| 2008/0147187 A1 | 6/2008 | Bollinger et al. |
| 2009/0084491 A1 | 4/2009 | Uthgenannt et al. |
| 2010/0057211 A1 | 3/2010 | Cuckler et al. |
| 2010/0131068 A1 | 5/2010 | Brown et al. |

OTHER PUBLICATIONS

Augmentation Patella, Zimmer, http://www.zimmer.com/ctl?template=MP&action=&id=698&op=global&pr=Y (printed Mar. 8, 2006).

NexGen All Poly Patella, Zimmer, Inc., Mar. 8, 2006 (1 page).

NexGen Complete Knee Solution System—"Primary Porous Patella with Trabecular Metal" copyright 2001 Zimmer, Inc., (2 sheets).

* cited by examiner

REVISION PATELLA PROSTHESIS

FIELD

The present disclosure generally relates to prosthetic implants and more specifically to an artificial patella component that is adapted to be secured to a natural patella component.

BACKGROUND

The statements in this section merely provide background information related to the present disclosure and may not constitute prior art.

In some instances, the knee joint may undergo degenerative changes due to multiple etiologies. In some examples, when these degenerative changes are advanced, irreversible and unresponsive to non-operative management, it may ultimately become necessary to replace some or all of a natural knee joint with artificial knee joint prosthetics. On some of these occasions, it may be necessary to surgically implant within the natural patella an artificial patella component, which then articulates with the patellar femoral groove of a natural femur or a replacement femoral component.

SUMMARY

A knee prosthesis assembly can comprise a patella prosthesis adapted to be secured to a natural patella portion having an anterior surface and a posterior surface. An articulating portion can have a posteriorly facing portion and an anteriorly facing portion. The posteriorly facing portion can have a spherical articular surface. A porous portion can have a first portion that engages the anteriorly facing portion and a second portion that engages the natural patella portion. A fastener can pass entirely through a passage formed at a centermost portion of the natural patella portion from the anterior surface to the posterior surface and into a bore defined in the centermost portion of the porous portion to securably engage the porous portion.

According to additional features, the fastener can define a head portion and a shank portion. The head portion can define a first diameter and the passage can define a second diameter. The first diameter can be greater than the second diameter. The shank of the fastener can threadably engage the porous portion. According to additional features, a washer can be disposed between the head portion and the natural patella. The washer can define a third diameter. The third diameter can be greater than the first diameter. According to some examples, the porous portion can comprise porous metal. The articulating portion can include a dome-shaped portion that is formed of ultra-high molecular weight polyethylene (UH-MWP). The fastener and the washer can be formed of resorbable material. A compression force applied to the fastener can be dispersed over the anterior surface of the natural patella component through the washer.

A method of securing a patella prosthesis to a natural patella having an anterior surface and a posterior surface can include shaping the natural patella to mate with the patella prosthesis. A hole can be formed in a center of the natural patella extending from the anterior to the posterior surface of the natural patella. The patella prosthesis can be engaged to the natural patella and a fastener can pass through the natural patella to the patella prosthesis.

According to additional features, the method can include passing the securing member through a washer and locating the washer between the anterior surface of the natural patella and a head of the securing member. The method can also comprise driving the fastener into the porous portion, such that a compressive force is distributed across the anterior surface of the natural patella and through the washer.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
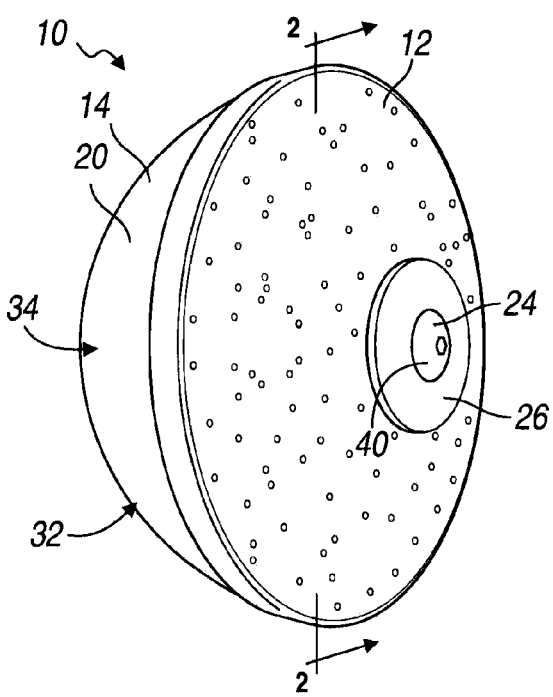
FIG. 1 is a medial perspective view of a patella including an artificial patella component and a natural patella component according to the present teachings.

The following description is merely exemplary in nature and is not intended to limit the present disclosure, application, or uses. It should be understood that throughout the drawings, corresponding reference numerals indicate like or corresponding parts and features.

Figure 2:
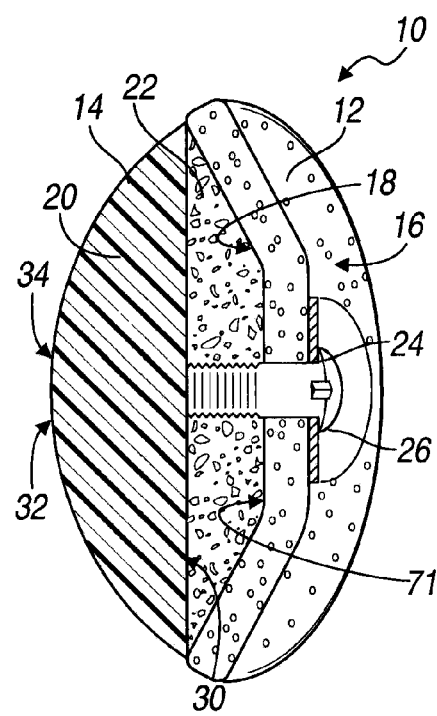
FIG. 2 is a perspective cross-sectional view of the patella taken along line 2-2 of FIG. 1.
Figure 3:
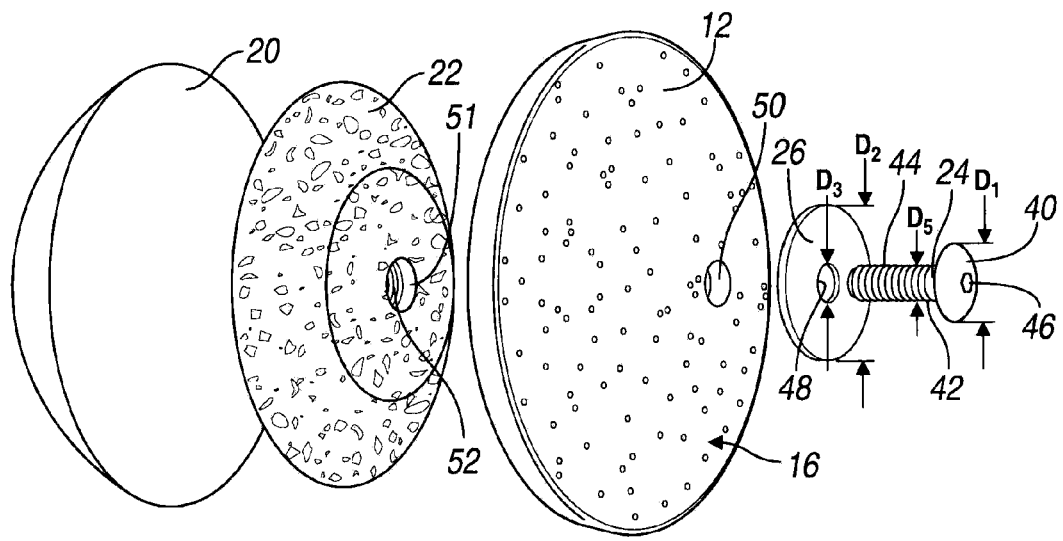
FIG. 3 is an exploded perspective view of the patella of FIG. 1.

With initial reference to FIGS. 1-3, a patella assembly constructed in accordance to the present teachings is shown and generally identified at reference numeral 10. The patella assembly 10 can generally comprise a natural patella portion 12 and an patella implant component or prosthesis 14 secured to the natural patella 12. The natural patella portion 12 can generally define an anterior surface 16 and a posterior surface 18. The artificial patella component 14 can generally comprise a dome-shaped portion 20, a porous portion 22, a securing member or fastener 24, and a washer 26.

Figure 4:
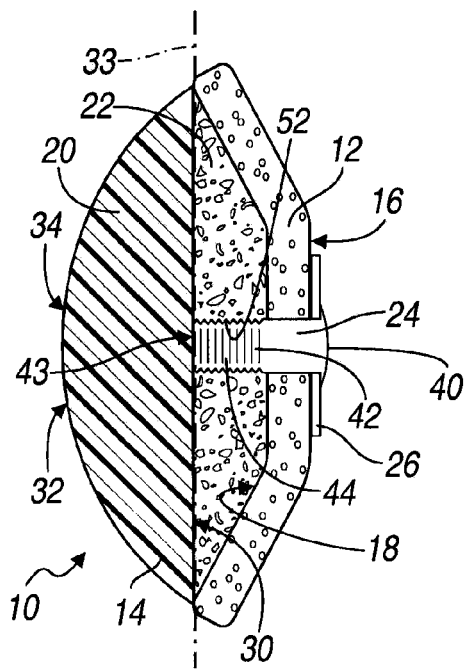
FIG. 4 is a cross-sectional view of the patella taken along line 2-2 of FIG. 1.
Figure 5:
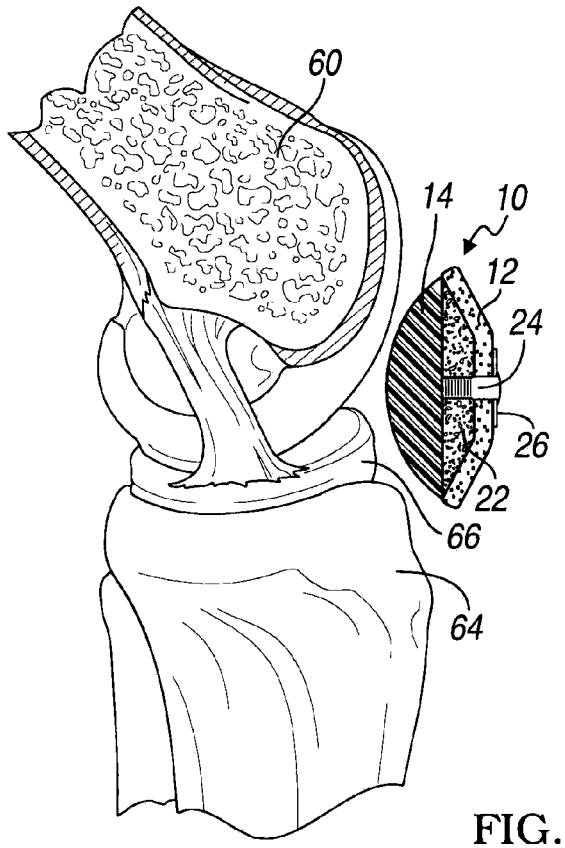
FIG. 5 is a medial view of an exemplary femur and tibia shown with the patella of FIG. 1 shown adjacent to a patellar track of the femur.

The dome-shaped portion 20 can generally define an anteriorly facing face or portion 30 and a posteriorly facing portion 32. The anteriorly facing portion 30 extends along an anterior-most surface of the dome-shaped portion 20 at an anterior plane 33 (FIG. 4). The posteriorly facing portion 32 can define an articular surface 34. The porous portion 22 can be located against the anteriorly facing portion 30 of the dome-shaped portion 20. In one example, the porous portion 22 may comprise porous metal, such as porous titanium, for example. Other exemplary porous metal materials can be used, such as those described in commonly owned and copending U.S. Ser. No. 11/357,929, filed Feb. 17, 2006, entitled "Method and Apparatus for Forming Porous Metal Implants", which is expressly incorporated by reference.

With specific reference to FIG. 3, the fastener 24 can define a head 40 and a shank 42. The shank 42 can extend from the head 40 to a terminal end 43 (FIG. 4). In one example, the shank 42 can define threads 44. The head 40 can define a gripping or driving portion 46. While the gripping portion 46 is represented in the drawings as a hex-head receptacle, other geometries and/or configurations may be employed. The head 40 of the fastener 24 can define a first diameter D1. The washer 26 can define an outer diameter D2. The washer 26 can define a bore 48 having an inner diameter D3. In one example, the diameter D3 can be slightly larger than a diameter D5 of the shank 42. In one example, the diameter D5 of the shank 42 can be substantially about 3 mm to about 4 mm.

A passage 50 can be formed through the natural patella portion 12 from the anterior surface 16 to the posterior surface 18. In one example, the porous portion 22 can define a bore 51 having threads 52 for threadably mating with the threads 44 defined on the fastener 24.

Figure 8:
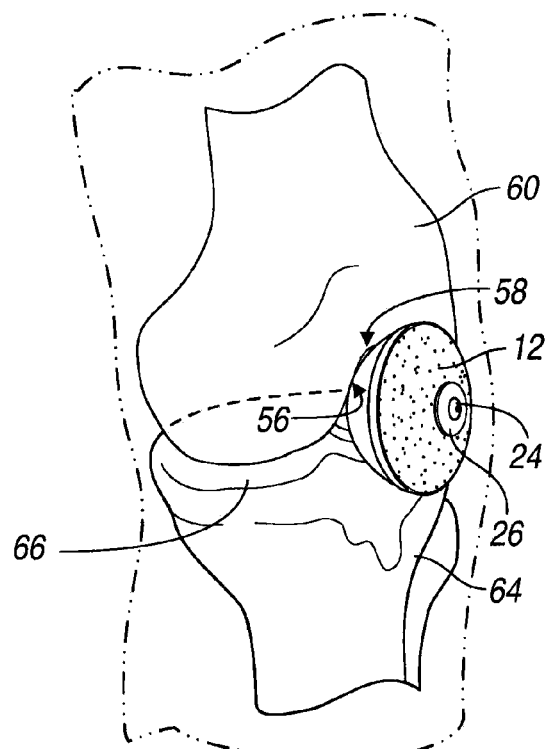
FIG. 8 is a medial perspective view of the exemplary knee of FIG. 7.

As will be described in greater detail, the artificial patella component 14 can be attached to the natural patella portion 12, so as to provide an articulating surface between the patella 10 and adjacent femur. More specifically, the artificial patella component 14 having the dome-shaped portion 20 and articular surface 34 can be shaped in a general spherical manner, which is operable to articulate with a patello-femoral groove 56 (see FIG. 8) defined in an anterior condylar portion 58 of a natural femur 60 or alternatively a femoral component 62 (see FIG. 9). As can be appreciated, the spherical shape of the articular surface 34 of the artificial patella component 14 can permit the patella 10 to remain relatively stationary with respect to the natural femur 60 (or femoral component 62) and a natural tibia 64 and meniscus 66 (or tibial component 76 and bearing liner 78, FIG. 9) as flexion of the knee joint occurs.

With reference now to FIG. 4, additional features of the present disclosure will be described. According to one example of the instant disclosure, the fastener 24 can be located at a centermost portion through the natural patella portion 12. According to one example, the head 40 and the washer 26 can sit proud (in a position generally raised from the anterior surface 16 of the natural patella portion 12). According to the present teachings, the fastener 24 can be the sole mechanical fastening feature that couples the artificial patella 14 with the natural patella portion 12. By locating the fastener 24 at a centermost portion through the natural patella portion 12, a compression force applied to the fastener 24 can be generally dispersed over the anterior surface 16 of the natural patella portion 12 through the washer 26. The present configuration can therefore provide a simple and robust patella assembly 10 without the need for supplemental fasteners such as those located elsewhere around the natural patella portion 12.

According to various examples, the fastener 24 and/or the washer 26 can be formed of resorbable material. In one example, the shank 42 of the fastener 24 can define a diameter of substantially about 3-7 mm. The dome-shaped portion 20 can be formed of a polymer, such as ultra-high molecular weight polyethylene (UHMWP).

A method of securing the artificial patella component 14 to the natural patella portion 12 according to one example will now be described. At the outset, the natural patella portion 12 can be measured to determine a suitable size and shape of an artificial patella component 14. In one example, the porous portion 22 can be secured to the dome-shaped portion 20, such as by way of mechanical fastening and/or chemical bonding. Exemplary mechanical fastening can include a ring lock arrangement such as disclosed in commonly owned U.S. Pat. No. 6,416,553, which is expressly incorporated herein by reference. Other methods can include a thermal press-fit between the porous portion 22 and the dome-shaped portion 20. It is also appreciated that while the interface between the dome-shaped portion 20 and the porous portion 22 is shown as generally planar, it may be non-planar. In some examples, the porous portion 22 can be secured to the anteriorly facing portion 30 prior to implantation. In other examples, the porous portion 22 can be secured to the anteriorly facing portion 30 of the artificial patella component 14 intraoperatively.

In some examples, it may be suitable to resurface and/or reshape the natural patella portion 12 to provide a desirable anterior surface 16 and/or posterior surface 18. In some examples, it may be desirable to resurface the posterior surface 18 of the natural patella portion 12 to match the profile of the porous portion 22, such that the porous portion 22 will nest with a recess 71 formed in the porous portion 12. Alternatively, or in addition to, it may be desirable to reshape and/or resurface the porous portion 22 to obtain a desirable profile for mating with the posterior surface 18 of the natural patella portion 12.

Figure 6:
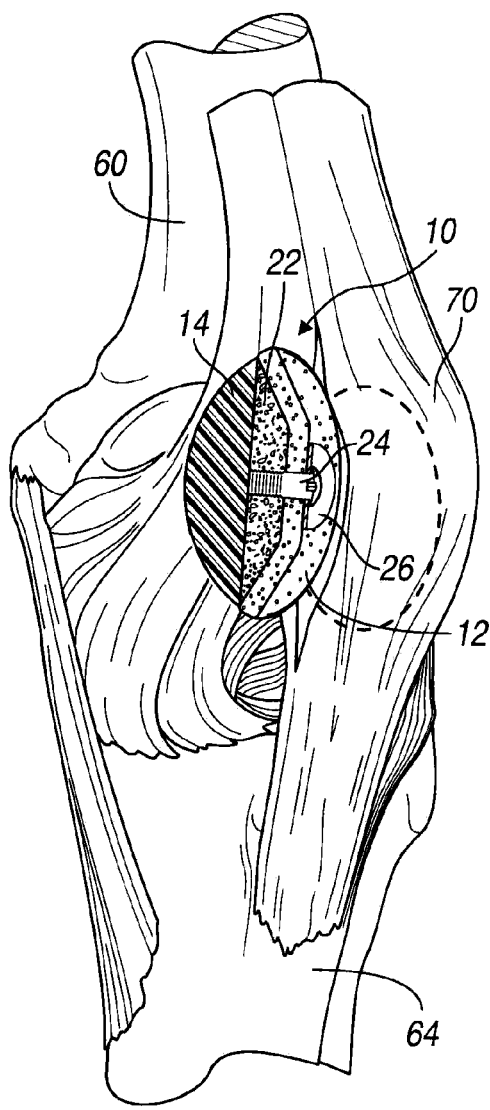
FIG. 6 is an exemplary knee shown with the patella of FIG. 1 positioned with respect to a patellar tendon.
Figure 7:
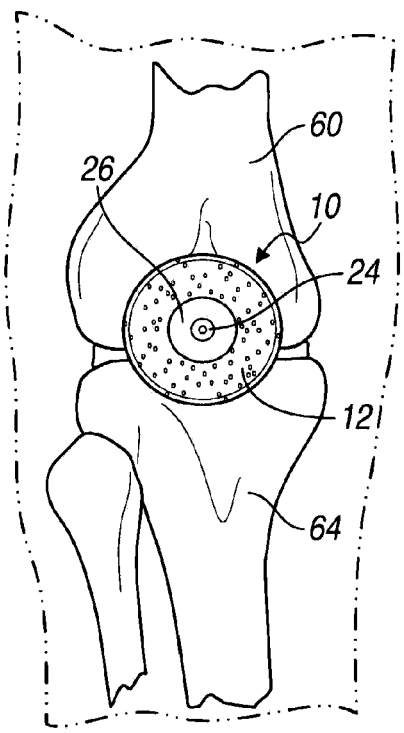
FIG. 7 is an anterior view of an exemplary knee including the patella of FIG. 1.

The shank 42 of the fastener 24 can be located through the bore of the washer 26 and through the passage 50 of the natural patella portion 12. Once a distal tip of the shank 42 passes entirely through the natural patella portion 12, the threads 44 can be cooperatively mated with the threads 52 defined in the bore 51 of the porous portion 22. In this regard, the shank 42 can act as the sole mechanical fastening member between the natural patella portion 12 and the porous portion 22. The fastener 24 can then be driven into a position, such as shown in FIG. 4 where the head 40 of the fastener 24 sits flush onto the washer 26 that in turn sits flush onto the anterior surface 16 of the natural patella portion 12. In this position, the terminal end 43 of the shank 42 contacts the anteriorly facing portion 30. In this regard, the fastener 24, the natural patella portion 12 and the porous portion 22 are all adapted to be located exclusively on an opposite side of the anterior plane 33 than the dome-shaped portion 20 (FIG. 4). In one example, the fastener 24 can be located as described above intraoperatively with a patellar tendon 70 displaced medially or laterally, such as shown in FIG. 6.

Figure 9:
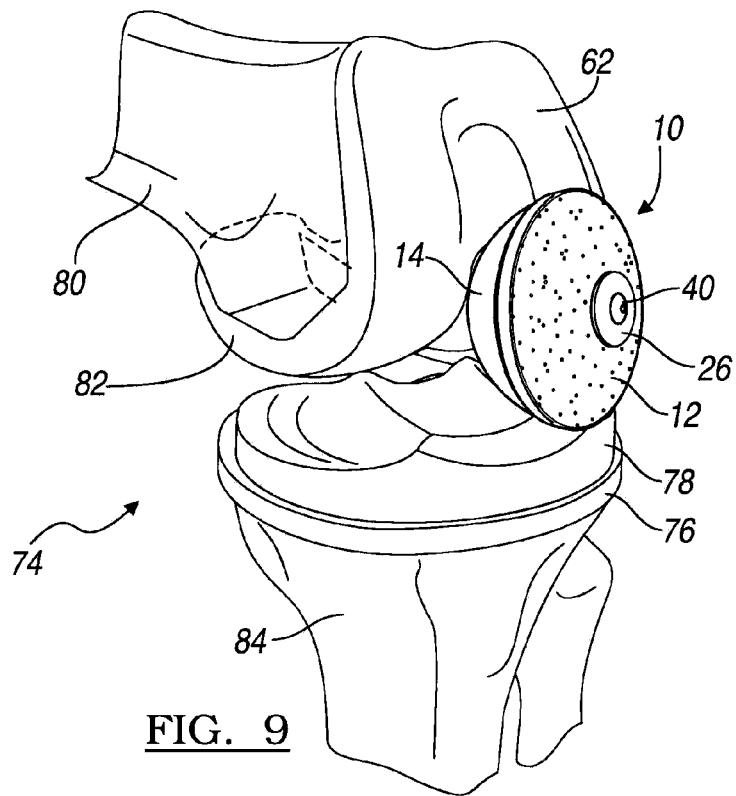
FIG. 9 is a medial perspective view of a knee joint prosthesis including a femoral component, a tibial component, a liner and the patella of FIG. 1.

With reference now to FIG. 9, the patella 10 can be used as part of a total knee prosthesis 74. In one example, the total knee prosthesis 74 can include the femoral component 62, the tibial component 76, and the bearing liner 78. As is known, the femoral component 62 can be rigidly connected to a distal end of a femur 80 after the femur 80 has been resected in a manner, which is well known in the art. The femoral component 62 can include a condylar portion 82, which engages the bearing liner 78. The tibial component 76 can be connected to a proximal end of a tibia 84 by any suitable method. The bearing liner 78 can be made from any suitable material, such as ultra-high molecular weight polyethylene (UHMWP). The patella assembly 10 can be a part of any knee joint, such as, but not limited to, cruciate retaining (CR), posterior stabilized (PS) and fully constrained (FC).

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, the specification and the following claims.

What is claimed is:

1. A knee prosthesis assembly comprising:
a patella prosthesis adapted to be secured to a natural patella portion having an anterior surface and a posterior surface, said patella prosthesis comprising:
an articulating portion having a posteriorly facing portion including a posteriorly facing articulating surface that is configured to articulate with a patello-femoral groove in a femur or a femoral component and an anteriorly facing portion having an anterior-most surface that extends along an anterior plane;
a porous portion having a first portion that engages said anteriorly facing portion at said anterior plane and a second portion that is adapted to engage said natural patella portion; and
a fastener that is adapted to pass entirely through a passage formed at a centermost portion of said natural patella portion from said anterior surface to said posterior surface and into a bore defined in a centermost portion of said porous portion to securably engage said porous portion wherein a terminal end of said fastener contacts said anterior-most surface of said articulating portion, the fastener occupies a space exclusively on one side of said anterior plane.

2. The knee prosthesis assembly of claim 1; wherein said fastener defines a head portion and a shank portion said head portion defining a first diameter and wherein said passage defines a second diameter, said first diameter being greater than said second diameter.

3. The knee prosthesis assembly of claim 2, wherein said shank portion of said fastener threadably engages said porous portion.

4. The knee prosthesis assembly of claim 2, further comprising a washer adapted to be disposed between said head portion and said natural patella portion.

5. The knee prosthesis assembly of claim 4, wherein said washer defines a third diameter, said third diameter being greater than said first diameter.

6. The knee prosthesis assembly of claim 4, wherein said fastener and said washer are formed of resorbable material.

7. The knee prosthesis assembly of claim 4, wherein a compression force applied to said fastener is adapted to be dispersed over said anterior surface of said natural patella portion through said washer.

8. The knee prosthesis assembly of claim 2, wherein said shank portion of said fastener is substantially about 3 to about 4 mm in diameter.

9. The knee prosthesis assembly of claim 2, wherein said head portion is adapted to sit at a position raised anteriorly relative to said anterior surface of said natural patella portion.

10. The knee prosthesis assembly of claim 1, wherein said porous portion comprises porous metal.

11. The knee prosthesis assembly of claim 1, wherein said articulating portion is dome-shaped and formed of ultra-high molecular weight polyethylene (UHMWP).

12. The knee prosthesis assembly of claim 1, further comprising:
the femoral component defining the patello-femoral groove; and
a tibial component, wherein the patella prosthesis is adapted to ride along the patello-femoral groove.

13. A knee prosthesis assembly adapted to be secured to a natural patella portion having an anterior surface and a posterior surface, said knee joint prosthesis assembly consisting essentially of:
an articulating portion defining a posteriorly facing articulating surface that is configured to articulate with a patello-femoral groove in a femur and an anteriorly facing engaging surface that extends along an anterior plane on an anterior-most surface of the articulating portion;
a porous portion engaged to said anteriorly facing engaging surface at said anterior plane; and
a securing member having a shank portion that extends from a head portion to a terminal end, wherein said shank portion is adapted to extend through an opening formed in the natural patella portion from said anterior surface to said posterior surface and threadably engage said porous portion, said shank portion adapted to extend through a centralized location in the natural patella portion and act as a sole mechanical fastening member between the natural patella portion and said porous portion wherein said terminal end of said shank portion contacts said anterior-most surface of said anteriorly facing engaging surface.

14. The knee prosthesis assembly of claim 13, wherein said head portion defines a first diameter and said opening defines a second diameter, said first diameter being greater than said second diameter.

15. The knee prosthesis assembly of claim 13, wherein said porous portion comprises porous metal.

16. The knee prosthesis assembly of claim 13, wherein said articulating portion is formed of ultra-high molecular weight polyethylene (UHMWP).

17. The knee prosthesis assembly of claim 13, wherein said securing member is formed of resorbable material.

18. The knee prosthesis assembly of claim 13, further comprising a washer adapted to be disposed between said head portion and the natural patella portion wherein a compression force applied to said securing member is adapted to be dispersed over said anterior surface of the natural patella portion through said washer.

19. The knee prosthesis assembly of claim 13, wherein said shank portion has a threaded portion that threadably engages said porous portion and a non-threaded portion that is adapted to align through said opening in the natural patella.

20. A knee prosthesis assembly comprising:
a patella prosthesis adapted to be secured to a natural patella portion having an anterior surface and a posterior surface, said patella prosthesis comprising:
an articulating portion having a posteriorly facing portion and an anteriorly facing portion, said anteriorly facing portion having an anterior plane on an anterior-most surface, said articulating portion having an articulating surface configured to articulate with a patello-femoral groove in a femur;
a porous portion having a first portion that engages said anteriorly facing portion and a second portion that is adapted to engage said natural patella portion; and
a fastener that is adapted to pass entirely through a passage formed at a centermost portion of said natural patella portion from said anterior surface to said posterior surface and into a bore defined in a centermost portion of said porous portion to securably engage said porous portion, said fastener having a head portion and a shank portion, said shank portion including a threaded portion and a non-threaded portion, said threaded portion threadably engaging said porous portion, said non-threaded portion adapted to be aligned with said passage in said natural patella; and
wherein said porous portion, said fastener and said natural patella are all adapted to be located exclusively on an opposite side of said anterior plane than said articulating portion.

21. The knee prosthesis assembly of claim 20, wherein said shank portion has a terminal end that contacts said anterior-most surface of said articulating portion.

\* \* \* \* \*